United States Patent
Ikebukuro et al.

(10) Patent No.: US 8,143,004 B2
(45) Date of Patent: Mar. 27, 2012

(54) METHOD OF ASSAYING TARGET SUBSTANCE IN SAMPLE, APTAMER MOLECULE METHOD OF CONSTRUCTING THE SAME

(75) Inventors: Kazunori Ikebukuro, Fuchu (JP); Koji Sode, Fuchu (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 143 days.

(21) Appl. No.: 12/443,053

(22) PCT Filed: Sep. 27, 2007

(86) PCT No.: PCT/JP2007/068767
§ 371 (c)(1),
(2), (4) Date: Mar. 26, 2009

(87) PCT Pub. No.: WO2008/038696
PCT Pub. Date: Apr. 3, 2008

(65) Prior Publication Data
US 2010/0021899 A1    Jan. 28, 2010

(30) Foreign Application Priority Data

Sep. 27, 2006   (JP) .................................. 2006-262048
Sep. 27, 2006   (JP) .................................. 2006-262253

(51) Int. Cl.
*C12Q 1/68*    (2006.01)
(52) U.S. Cl. ...................................... 435/6.11
(58) Field of Classification Search .................. 435/6.11
See application file for complete search history.

(56) References Cited

U.S. PATENT DOCUMENTS

| | | | |
|---|---|---|---|
| 7,727,721 B2* | 6/2010 | Pierce et al. ...................... | 435/6 |
| 2005/0089864 A1* | 4/2005 | Li et al. .............................. | 435/6 |
| 2007/0166740 A1* | 7/2007 | Heil et al. .......................... | 435/6 |
| 2008/0020939 A1* | 1/2008 | Stanton et al. .................... | 506/8 |

FOREIGN PATENT DOCUMENTS

| | | | |
|---|---|---|---|
| JP | 2003-294679 A | 10/2003 | |
| JP | 2003-294680 A | 10/2003 | |
| JP | 2003-294681 A | 10/2003 | |
| WO | WO 2007/086403 A1 | 8/2007 | |

OTHER PUBLICATIONS

Nutiu, et al. (2003) Structure-Switching Signaling Aptamers, J. Am. Chem. Soc., v.125(16):4771-8.*
Ogasawara, D., et al. (2009) Detection System Based on the Conformational Change in an Aptamer and Its Application to Simple Bound/Free Separation, Biosensors and Bioelectronics, v.24:1372-6.*
Gopinath, "Methods developed for SELEX", Analytical & Bioanalytical Chemistry, (2007), vol. 387, No. 1, pp. 171-182.
Hamaguchi et al., "Aptamer beacons for the direct detection of proteins", Analytical Biochemistry, (2001), vol. 294, pp. 126-131.
Ikebukuro et al., "A novel method of screening thrombin-inhibiting DNA aptamers using an evolution-mimicking algorithm", Nucleic Acids Research, (2005) vol. 33, No. 12, e108.
Ikebukuro et al., "Development of aptamer based protein detection system using DNA immolibized support for bound/free separation", The Electrochemical Society of Japan, Apr. 1, 2006, p. 231, 3J07.
Ikebukuro et al., "Novel electrochemical sensor system for protein using the aptamers in sandwich manner", Biosensors and Bioelectronics, (2005), vol. 20, No. 10, pp. 2168-2172.
Noda et al., "Generation of RNA aptamers binding to abnormal prion proteins", Japanese Society of Veteriany Science, Aug. 31, 2006, p. 79, DV-01.
Noda et al., "Isolation of RNA aptamers binding to normal prion proteins", Japanese Society of Veteriany Science, Aug. 1, 2004, p. 98, DV-49.
Nutiu et al., "In vitro selection of structure-switching signaling aptamers", Agnew. Chem. Int. Ed., vol. 144, No. 7, pp. 1061-1065, Feb. 4, 2005.
Yoshida et al., Homogeneous DNA sensing using enzyme-inhibiting DNA aptamers, Biochemical and Biophysical Research Communications, Aug. 17, 2006, vol. 348, Issue 4968, No. 1, pp. 245-252.
Tuerk et al., "Systematic evolution of ligands by exponential enrichment: RNA ligands to bacteriophage T4 DNA polymerase", Science 3, Aug. 1990, vol. 249, No. 4968, pp. 505-510, Abstract Only.

* cited by examiner

*Primary Examiner* — Brian Whiteman
(74) *Attorney, Agent, or Firm* — Birch, Stewart, Kolasch & Birch, LLP (57) ABSTRACT

A method for measuring a test substance whereby the test substance in a sample can be specifically measured without using an antibody against the test substance; an aptamer molecule used therefor; and a method for creating the aptamer are disclosed. An aptamer capable of hybridizing with an oligonucleotide when it is bound to a test substance, but is incapable of hybridizing with the oligonucleotide when it is not bound to the test substance, is utilized. The aptamer is brought into contact with a sample, and the aptamer bound to the test substance is brought into contact with an immobilized oligonucleotide which hybridizes with the aptamer, to bind the aptamer to a solid phase, followed by measurement of the aptamer immobilized on the solid phase.

8 Claims, 4 Drawing Sheets

SEQUENCE LISTING

```
<160> NUMBER OF SEQ ID NOS: 7

<210> SEQ ID NO 1
<211> LENGTH: 66
<212> TYPE: DNA
<213> ORGANISM: Artificial Sequence
<220> FEATURE:
<223> OTHER INFORMATION: Synthetic DNA random library for preparing
      aptamer
<220> FEATURE:
<221> NAME/KEY: misc_feature
```

```
<222> LOCATION: (19)..(48)
<223> OTHER INFORMATION: randomly selected nucleotide

<400> SEQUENCE: 1
ataccagtct attcaattnn nnnnnnnnnn nnnnnnnnnn nnnnnnnnag atagtatgtg    60
caatca                                                              66

<210> SEQ ID NO 2
<211> LENGTH: 66
<212> TYPE: DNA
<213> ORGANISM: Artificial Sequence
<220> FEATURE:
<223> OTHER INFORMATION: Synthetic aptamer Clone 4-9

<400> SEQUENCE: 2
ataccagtct attcaattgg gcccttttct gtgtctttct gtgcccttag atagtatgtg    60
caatca                                                              66

<210> SEQ ID NO 3
<211> LENGTH: 9
<212> TYPE: DNA
<213> ORGANISM: Artificial Sequence
<220> FEATURE:
<223> OTHER INFORMATION: Synthetic hybridization region with
      immobilized oligonucleotide

<400> SEQUENCE: 3 gttcggcac                                                            9

<210> SEQ ID NO 4
<211> LENGTH: 61
<212> TYPE: DNA
<213> ORGANISM: Artificial Sequence
<220> FEATURE:
<223> OTHER INFORMATION: Synthetic aptamer CaAp-1

<400> SEQUENCE: 4
agtctacaga attgggccct tttctgtgtc tttctgtgcc cttagatagt atgtgcaatc    60
a                                                                   61

<210> SEQ ID NO 5
<211> LENGTH: 60
<212> TYPE: DNA
<213> ORGANISM: Artificial Sequence
<220> FEATURE:
<223> OTHER INFORMATION: Synthetic aptamer CaAp-2

<400> SEQUENCE: 5
ccagacagaa ttgggccctt ttctgtgtct ttctgtgccc ttagatagta tgtgcaatca    60

<210> SEQ ID NO 6
<211> LENGTH: 9
<212> TYPE: DNA
<213> ORGANISM: Artificial Sequence
<220> FEATURE:
<223> OTHER INFORMATION: Synthetic immobilized oligonucleotide

<400> SEQUENCE: 6 gtgccgaac                                                            9

<210> SEQ ID NO 7
<211> LENGTH: 59
<212> TYPE: DNA
<213> ORGANISM: Artificial Sequence
<220> FEATURE:
```

```
<223> OTHER INFORMATION: Synthetic aptamer CaAp-3

<400> SEQUENCE: 7
gttcggcact tgggcccttt tctgtgtctt tctgtgccct tagatagtat gtgcaatca      59
```

METHOD OF ASSAYING TARGET SUBSTANCE IN SAMPLE, APTAMER MOLECULE METHOD OF CONSTRUCTING THE SAME

TECHNICAL FIELD

The present invention relates to a method for measuring a test substance in a sample, an aptamer molecule and a method for creating the aptamer.

BACKGROUND ART

Measurement of a test substance such as a protein in a sample is currently carried out mainly by an immunoassay. As the immunoassay, various methods are known and practically applied, any of which methods utilizes a specific antibody against the test substance. Although creation of the specific antibody against the test substance can be carried out by a conventional method, it is laborious, so that the specific antibody is expensive.

On the other hand, aptamers which specifically bind to an arbitrary molecules are known. An aptamer which specifically binds to a desired target molecule can be created by a method called SELEX (Systematic Evolution of Ligands by EXponential Enrichment) (Non-patent Literature 1). In this method, the target molecule is immobilized on a carrier, to which a nucleic acid library comprising nucleic acids having vast kinds of random base sequences is added, and nucleic acids which bind to the target molecule are collected, which nucleic acids are then amplified by PCR, followed by addition of the amplified nucleic acids again to the carrier on which the target molecule is immobilized. By repeating this process about 10 times, aptamers having high binding abilities to the target molecule are concentrated, and the sequences thereof are determined to obtain aptamers recognizing the target molecule. The above nucleic acid library can be easily prepared by binding nucleotides randomly by an automated chemical synthesizer for nucleic acids. Thus, by the method using a library of nucleic acids having random base sequences, and which positively utilizes contingency, an aptamer which specifically bind to an arbitrary target substance can be created. An aptamer usually has a single-stranded region, and creation of an aptamer by a modified SELEX method is also known, wherein a complementary oligonucleotide can hybridize with the single-stranded region when the aptamer is not bound to the target substance, but cannot hybridize therewith when the aptamer is bound to the target substance (Non-patent Literature 2).

Patent Literature 1: JP 2003-294679 A
Patent Literature 2: JP 2003-294680 A
Patent Literature 3: JP 2003-294681 A
Non-patent Literature 1: Tuerk, C. and Gold L. (1990), Science, 249, 505-510
Non-patent Literature 2: Angew. Chem. Int. Ed. 2005, 44, 1061-1065
Non-patent Literature 3: Kazunori Ikebukuro et al., Nucleic Acids Research, 33(12), e108

DISCLOSURE OF THE INVENTION

Problems to be Solved by the Invention

An object of the present invention is to provide a novel method for measuring a test substance, by which the test substance in a sample can be specifically measured without using an antibody against the test substance.

Another object of the present invention is to provide a novel aptamer molecule having new characteristics useful for measurement of a target substance, and a method for creating it.

Means for Solving the Problems

As a result of intensive study, the present inventors discovered that a test substance in a sample can be measured by utilizing an aptamer which can hybridize with an oligonucleotide when it is bound to the test substance, but cannot hybridize with the oligonucleotide when it is not bound to the test substance; bringing the aptamer into contact with the sample; bringing the aptamer bound to the test substance into contact with the immobilized oligonucleotide to bind the aptamer to a solid phase; and measuring the aptamer bound to the solid phase; thereby accomplishing the present invention.

That is, the present invention provides a method for measuring a test substance in a sample, the method comprising: simultaneously or sequentially bringing an aptamer, the test substance in the sample and a solid phase on which an oligonucleotide is immobilized, into contact with each other, the aptamer having a property to bind to the test substance, the aptamer hybridizing with the oligonucleotide immobilized on the solid phase when it is bound to the test substance, the aptamer being incapable of binding to the immobilized oligonucleotide when it is not bound to the test substance; and measuring the aptamer bound to the solid phase, after washing. The present invention also provides a solid phase for carrying out the method according to the present invention, the solid phase comprising a carrier on which the oligonucleotide is immobilized.

As a result of intensive study, the present inventors also discovered that, by adding or inserting a hybridization region which hybridizes with an oligonucleotide to or into an aptamer molecule capable of binding to a target substance and of hybridizing with an oligonucleotide when it is bound to the target substance, which hybridization region is designed such that at least a part thereof has a base sequence complementary to another region in the aptamer molecule, an aptamer molecule can be obtained wherein the hybridization region is subjected to intramolecular hybridization in the absence of the target substance and therefore the region is incapable of hybridizing with the oligonucleotide, whereas, in the presence of the target substance, the intramolecular hybridization is unraveled to enable hybridization with the oligonucleotide.

That is, the present invention provides an aptamer molecule having a structure-switching property, which is made of a single-stranded nucleic acid, which is capable of binding to a target substance, and which can hybridize with an oligonucleotide when it is bound to the target substance; wherein at least a part of the region that hybridizes with the oligonucleotide has a base sequence complementary to another part in the aptamer molecule; wherein in the absence of the target substance, the at least a part of the region which hybridizes with the oligonucleotide intramolecularly hybridizes with the another part complementary thereto, thereby the hybridization with the oligonucleotide does not occur; and wherein in the presence of the target substance, the intramolecular hybridization is unraveled to expose the region that hybridizes with the oligonucleotide, thereby the aptamer molecule is capable of hybridizing with the oligonucleotide. The present invention also provides a method for creating an aptamer molecule having a structure-switching property, the method comprising the steps of: preparing modified aptamer molecules having a region which hybridizes with an oligonucleotide, the region being added to or inserted in an aptamer molecule that is made of a single-stranded nucleic acid and is capable of binding to a target substance; and screening a modified aptamer molecule which retains binding capacity to the target substance, which is capable of hybridizing with the oligonucleotide when it is bound to the target substance, and which is not capable of hybridizing with the oligonucleotide when it is not bound to the target substance; wherein at least a part of the region that hybridizes with the oligonucleotide has a base sequence complementary to another part in the aptamer molecule; wherein in the absence of the target substance, the at least a part of the region which hybridizes with the oligonucleotide intramolecularly hybridizes with the another part complementary thereto, thereby the hybridization with the oligonucleotide does not occur; and wherein in the presence of the target substance, the intramolecular hybridization is unraveled to expose the region that hybridizes with the oligonucleotide, thereby the aptamer molecule is capable of hybridizing with the oligonucleotide.

Effects of the Invention

By the present invention, a novel measuring method capable of specifically measuring a test substance without using an antibody against the test substance, and a solid phase for the method was provided. Since aptamers can be produced using an automated chemical synthesizer, they can be prepared much more easily and inexpensively than specific antibodies. Thus, by the present invention, specific measurement of various test substances can be carried out more inexpensively than by the conventional methods. Accordingly, the present invention is expected to make great contributions in various fields such as diagnosis of various diseases, quality inspections of foods and beverages, measurement of pollution by environmental toxic substances and the like.

Further, by the present invention, an aptamer molecule having a structure-switching property and a method for creating it were provided for the first time, which aptamer molecule is capable of hybridizing with a prescribed immobilized oligonucleotide in the presence of a target substance, but which aptamer molecule is incapable of hybridizing with the immobilized oligonucleotide in the absence of the target substance. By utilizing such an aptamer molecule having a structure-switching property, a target substance can be measured with a method similar to various well-known immunoassays.

BEST MODE FOR CARRYING OUT THE INVENTION

The test substances measured by the method of the present invention are not restricted at all as long as the aptamer which specifically binds thereto can be produced, and examples thereof include various proteins (including protein complexes such as glycoproteins and lipoproteins), saccharides (including polysaccharides, oligosaccharides and monosaccharides, as well as saccharide complexes such as glycolipids), lipids, nucleic acids, low molecular weight compounds and the like. As described above, the aptamer is created by the method positively utilizing contingency, and it is therefore possible to create aptamers which specifically bind to almost all the target molecules, respectively. Although the Examples below use an α-helix type prion (normal type prion, α-PrP) as the test substance, the test substance is not restricted thereto as described above, and preferred examples thereof include insulin and glucagon which serve as disease marker molecules; α-fetoprotein which serves as a liver cancer marker; CEA which serves as a marker for cancers of digestive organs; PSA which serves as a prostate cancer marker; CA125 which serves as an ovarian cancer marker; CA19-9 which serves as a pancreas cancer marker; an HIV virus antibody, anti-hepatitis C virus antibody and anti-hepatitis B virus antibody, which serve as markers for various infectious diseases; and the like. In the present invention, "measurement" includes quantification, semi-quantification and detection.

The aptamer used in the method of the present invention is an aptamer having a property to bind to a test substance, which aptamer hybridizes with an immobilized oligonucleotide when it is bound to the test substance, but which aptamer is incapable of binding to the immobilized oligonucleotide when it is not bound to the test substance. The aptamer used in the present invention is preferably the aptamer molecule of the present invention described below, but an aptamer other than the aptamer of the present invention described below can also be used in the method of the present invention as long as it is an aptamer satisfying the above requirements. The size of the aptamer used in the method of the present invention is not restricted, and usually about 30-mer to 100-mer, preferably about 50-mer to 70-mer (mer indicates the number of nucleotides). The aptamer may be either DNA or RNA, or another artificial nucleic acid, but is preferably DNA, which is chemically stable and capable of being synthesized easily by automated chemical synthesis.

The aptamer preferably comprises a loop-like single-stranded region when the aptamer is hybridized with the oligonucleotide, and the regions adjacent to the both ends of the single-stranded region, respectively, preferably form a double-stranded region. An aptamer is known to comprise the so called "stem-loop structure" like this in many cases, and also known to bind specifically to a test substance mainly through the single-stranded loop structure region. The size of the single-stranded region is not restricted, and usually about 8-mer to 25-mer. The sizes of the regions which are adjacent to the both ends of the single-stranded region and which form the double-stranded region are not restricted, and preferably 2 bp to 10 bp. The secondary structure of the aptamer can be determined easily by a conventional method using a computer. As a software for analysis of the secondary structure of the aptamer, well-known Mfold, for example, can be utilized, which software is freely available in the Mfold web server www.bioinfo.rpi.edu/applications/mfold/dna/).

The aptamer used in the present invention is preferably labeled so as to enable simple measurement of the aptamer bound to the solid phase described later. As for the label, well known labels conventionally used in immunoassays can be employed, and, for example, enzyme labels, fluorescent labels, chemiluminescent labels, radioactive labels, gold colloid labels and the like can be employed. These labels may be attached to the aptamer by a conventional method after preparing the aptamer, and the labeled aptamer can also be obtained by using, as a primer for PCR which is carried out during the preparation process of the aptamer by SELEX described below, a primer having a label attached to its end (the end corresponding to the end of the polynucleotide being amplified). The label is preferably attached to one end or its vicinity of the aptamer so as not to interfere with the specific binding between the aptamer and the test substance. Labeling of the aptamer is preferred since it makes measurement of the aptamer bound to the solid phase easy, but labeling is not indispensable because the aptamer bound to the solid phase can be measured by the surface plasmon resonance (SPR) method as described in the Examples below even in cases where the aptamer is not labeled.

The immobilized oligonucleotide which hybridizes with the above aptamer is not restricted as long as it is an oligonucleotide capable of binding the aptamer to the solid phase by hybridizing with the aptamer under measurement conditions (described below), and the oligonucleotide preferably comprises a region, which is complementary at least to a consecutive part in the aptamer, the size of the region being 4-mer to 25-mer, more preferably 8-mer to 25-mer. To achieve an aptamer, which has the property to hybridize with an oligonucleotide immobilized on a solid phase when it is bound to a test substance, but which is incapable of hybridizing with the immobilized oligonucleotide when it is not bound to the test substance (this property may be hereafter referred to as "structure-switching property"), the combination of the base sequence of the aptamer and the base sequence of the immobilized oligonucleotide can be appropriately designed. This will be described later in more detail.

The above oligonucleotide is used after being immobilized on a solid phase. That is, the oligonucleotide is used in the state of being immobilized on a solid carrier. A method to immobilize an oligonucleotide on a solid phase is well known. For example, by covalently bonding biotin to one end of an oligonucleotide while immobilizing avidin on a carrier, it is possible to bind the oligonucleotide to the carrier via the avidin-biotin bond, whereas the method is not restricted thereto, and the oligonucleotide can also be directly and covalently bound to the carrier by a method such as the glutaraldehyde crosslinking method. It may also be physically adsorbed on such as a membrane made of nylon or nitrocellulose which adsorbs DNA well. The oligonucleotide may also be directly bound to the carrier, or may be bound to the carrier via a low molecular weight compound such as biotin. Further, the oligonucleotide may also be bound to the carrier via a spacer. For example, a longer oligonucleotide comprising in its one end the oligonucleotide to be immobilized may also be prepared, the end, which is opposite to the oligonucleotide to be immobilized, being bound to the carrier via the above described biotin-avidin bond or the like. In this case, in the nucleic acid immobilized on the carrier, the polynucleotide moiety other than the oligonucleotide to be immobilized simply acts as a spacer, and therefore the base sequence and the size thereof are not restricted at all. As for the carrier used as the solid phase, one conventionally used for immobilization of nucleic acids can be used as it is. For example, avidin beads, wherein avidin was immobilized on beads made of a macromolecule such as a synthetic resin or agarose, are commercially available, and therefore a commercial product can be used as it is. Alternatively, a commercially available substrate for a DNA chip such as one made of glass, silicon, and a synthetic resin can also be used. As for the carrier like this, one in the form of a column, like one used in chromatography, or one in the form of a filter can also be employed in addition to ones in the form of beads or a plate. Alternatively, in cases where the measurement is carried out by SPR, a sensor chip for SPR can be used as the solid phase. Also in this case, as described above, the sensor chip, on which avidin or streptavidin was immobilized, is commercially available, and therefore, by binding biotin to one end of the oligonucleotide, the oligonucleotide can be immobilized on the sensor chip via the avidin-biotin bond.

The aptamer used in the present invention hybridizes with an immobilized oligonucleotide when it is bound to a test substance, but the aptamer is incapable of hybridizing with the immobilized oligonucleotide when it is not bound to the test substance. That is, the secondary structure and/or tertiary structure of the above aptamer change(s) between the state of being bound to the test substance and the state of being unbound thereto, and as a result, the aptamer hybridizes with the oligonucleotide when the aptamer is bound to the test substance, but the aptamer is incapable of hybridizing with the oligonucleotide when it is not bound to the test substance.

Such a structure-switching aptamer capable of binding to an arbitrary test substance can be created by first creating aptamers which bind to the test substance, by the above SELEX method or its modification mentioned below, and subsequently screening aptamers having the structure-switching property among the obtained aptamers. Alternatively, it can be created by creating an aptamer which binds to the test substance by the above SELEX method or its modification mentioned below; then intentionally modifying the obtained aptamer such that the above described structure-switching property is exerted; and checking the modified aptamer to confirm that it has the structure-switching property. The latter method is more preferred since, in this method, an aptamer having a desired structure-switching property can be effectively obtained, and the amount of the test substance used can be small (the test substance is often a valuable biological substance, and therefore the fact that only a small amount of a test substance is required is an advantageous feature). The method for the intentional modification of the aptamer will be described later in detail.

In either case, the aptamers which bind to the test substance are first created by the SELEX method or the modification thereof described below. Since the sizes of the aptamers are usually about 30-mer to 100-mer, a library of nucleic acids having random base sequences of about these sizes are synthesized by an automated nucleic acid synthesizer. In this case, although the full length of the nucleic acid may be a random base sequence, the both end regions of the nucleic acid may also be known base sequences, to make PCR simple when SELEX is carried out. In this case, PCR primers can be hybridized to the regions of these known sequences, respectively. The sizes of the regions which are located in the both end regions of the nucleic acid are not restricted, and usually about 10-mer to 25-mer. In the Examples below, a nucleic acid library of SEQ ID NO: 1 was synthesized automatically. Since "N" in SEQ ID NO:1 is an arbitrary base, a nucleic acid library comprising vast kinds of base sequences is formed. If the regions with which the primers hybridize are provided, it becomes unnecessary to determine the base sequence of the aptamer before PCR described later, so that the production process of the aptamer is simplified. However, since the flexibility of the sequence of the aptamer decreases instead, the regions may not be provided.

Subsequently, a test substance immobilized on a solid phase is provided, and the nucleic acid library produced as described above is reacted with the immobilized test substance. The immobilization of the test substance may be carried out simply by physical adsorption of the test substance on a solid phase such as a nitrocellulose membrane, nylon membrane, filter paper, and well of a polystyrene microtiter plate, and in cases where the test substance is a protein, it may also be carried out by covalently bonding the protein to the carrier by utilizing a carboxyl group or amino group of the test substance. The former is simpler. As the conditions of the reaction between the nucleic acid library and the test substance, the same conditions as in the actual measurement of the test substance are preferred, and therefore carrying out the reaction at room temperature is simple and preferred. The reaction time is not restricted, and usually about 1 minute to 30 minutes, preferably about 10 minutes to 20 minutes. Upon reacting with the test substance, aptamers which bind to the test substance are bound to the immobilized test substance and immobilized on the solid phase. On the other hand, nucleic acids which do not bind to the test substance are not bound to the solid phase, and therefore removed by washing.

After removing the nucleic acids which were not bound to the solid phase by washing, the aptamers bound to the immobilized test substance are eluted. The elution can be carried out for example by treating the solid phase with urea at a high concentration of about 6 M to 8 M. Eluted nucleic acids can be collected by a conventional method such as phenol extraction and/or phenol-chloroform extraction and ethanol precipitation. All the collected aptamers are those bound to the immobilized test substance.

Subsequently, PCR is carried out using the collected aptamers as templates, to amplify the aptamers. In cases where the nucleic acids which were automatically synthesized have the above described primer binding regions in the both end regions, PCR is carried out using those primers. In cases where such primer binding regions are not provided, the base sequences of the collected aptamers are determined, and a pair of PCR primers complementary to their both end regions is synthesized respectively, which primers are used for carrying out PCR. By carrying out asymmetric PCR (one of the pair of primers used in PCR is used in an excess amount), mainly single-stranded nucleic acids can be amplified. Alternatively, single-stranded nucleic acids (the strand which is not biotin-labeled) can be collected from the amplified double-stranded nucleic acids by using a biotin-labeled primer as one of the primers used in PCR; binding the amplified double-stranded nucleic acids to avidin beads; denaturing the nucleic acids in this state by NaOH or the like; and collecting the nucleic acids separated from the beads. By this, since only aptamers which bind to the immobilized test substance are amplified, and the numbers of molecules of the aptamers which bind well to the immobilized test substance and which serve as the templates in PCR are large, the percentages thereof in the amplified nucleic acid library become high.

Subsequently, using the library of the amplified aptamers as the nucleic acid library described above, the above series of steps, that is, a cycle of the series of the steps of: reaction with the immobilized test substance; washing; elution and collection of the aptamers; and amplification by PCR; is repeated about several times to ten and several times. By this, aptamers which bind well to the test substance are concentrated, and aptamers having high binding capacities to the test substance can be obtained.

The present inventors previously invented an improved SELEX, wherein aptamers are allowed to evolve in silico (Non-patent Literature 3). By application of the evolution in silico described in Non-patent Literature 3 to the above described method which is described in Non-patent Literature 2, it is possible to increase the efficiency of creation of desired aptamers. This method will be described later in more detail in the section explaining the method of creation of the aptamers of the present invention.

The present inventors also invented an improved SELEX, wherein aptamers having higher binding capacities with a test substance can be efficiently obtained in usual SELEX, and filed a patent application directed thereto (JP 2007-14292 A). By this improved SELEX, aptamers which bind to a desired test substance with high specificity can be created efficiently. This method will be described in the section explaining the method of creation of the aptamer molecules of the present invention.

Subsequently, the aptamers thus obtained are checked for whether or not they have a structure-switching property. The aptamer of the No. 1 ranking in terms of the binding capacity to the test substance is checked, and if it does not have a structure-switching property, the aptamer of the No. 2 ranking (that is, an aptamer whose ratio in the nucleic acid library after the amplification is second-ranked) is checked, and if it does not have a structure-switching property, the aptamer of the No. 3 ranking is checked, to find out an aptamer having a structure-switching property.

However, this method is not necessarily highly effective, and laborious, and there is the possibility that the amount of the required test substance becomes high. Thus, the present inventors invented a method to modify an aptamer intentionally such that a structure-switching property is obtained. This method will be described later in the section explaining the method of creation of the aptamer molecules of the present invention.

Using the above described immobilized oligonucleotide and aptamer, the method of the present invention can be carried out as follows. First, a test substance in a sample is allowed to contact the above aptamer. This can be carried out by mixing the sample with an aptamer solution and incubating the resulting mixture. When the test substance is quantified, it is preferred that the aptamer in an excess amount with respect to the expected amount of the test substance in the sample be allowed to react so as to bind the entire test substance to the labeled aptamer. The conditions of the incubation are not restricted, and incubation at room temperature is preferred because it is simple. The reaction time is usually about 1 minute to 30 minutes, preferably about 10 minutes to 20 minutes.

Subsequently, the mixed solution of the sample and aptamer is brought into contact with the above described immobilized oligonucleotide. This can be carried out by mixing the above described carrier, on which the oligonucleotide is immobilized, with the mixed solution of the sample and aptamer, and incubating the resulting mixture. Alternatively, in cases where the carrier on which the oligonucleotide is immobilized is in the form of a column or filter, it may also be carried out simply by allowing the mixture to pass through the column or filter. When the test substance is quantified, the immobilized oligonucleotide is preferably in an excess amount with respect to the expected amount of the test substance in the sample subjected to the measurement (that is, an amount, with which the total amount of the test substance in the sample subjected to the measurement can be bound to the immobilized oligonucleotide via the aptamer). The incubation is simply and preferably carried out at room temperature similarly to the condition employed in the modification of SELEX when the aptamer was created. The reaction time is not restricted, and usually about 1 minute to 30 minutes, preferably about 10 minutes to 20 minutes. After this incubation, the solid phase is washed to remove the aptamer which was not bound to the solid phase. In cases where the measurement is carried out by SPR, the above incubation is not necessary since SPR can measure the binding in real time.

If the test substance is contained in the sample, the test substance is bound to the aptamer. The aptamer bound to the test substance hybridizes with the immobilized oligonucleotide, and is bound to the solid phase as described above. On the other hand, the aptamers which did not bind to the test substance is removed by washing since it is not capable of hybridizing with the immobilized oligonucleotide.

In the next step, the aptamer bound to the solid phase is measured. As described above, the aptamer bound to the solid phase is the aptamer bound to the test substance, and therefore measurement of the aptamer bound to the solid phase allows measurement of the test substance in the sample.

The measurement of the aptamer bound to the solid phase can be carried out for example by SPR as described in the Examples below. In this case, the above method can be carried out by using a sensor chip for SPR, on which the oligonucleotide was immobilized, as the above solid phase. Alternatively, as described above, the aptamer bound to the solid phase can also be measured by using labeled aptamer and measuring the label bound to the solid phase. As for the label, any label which is conventionally used in immunoassays can be used as described above, and measurement thereof can also be carried out by conventional methods for these respective labels. For example, in cases where the label is a fluorescent label, the fluorescence intensity of the label bound to the solid phase is measured. In cases where the label is a chemiluminescent label or radioactive label, the luminescence intensity or intensity of radioactivity bound to the solid phase is measured. In cases where the label is an enzyme, a substrate necessary for an enzyme reaction is added, and the product yielded by the enzyme reaction is measured. In case of an enzyme which catalyzes an electrochemical reaction, a working electrode, counter electrode, and reference electrode are immersed in a solution to which a substrate of the enzyme was added, and the electromotive force induced between the working electrode and counter electrode is measured. This is the same as the measurement of an enzyme reaction using a conventional enzyme electrode, and can be carried out easily by a conventional method. In cases where the enzyme reaction product is a colored substance, the product can be measured by measuring the absorbance of the reaction solution. In cases where one desires to measure a label in the free state when the label bound to the solid phase is measured, the label may be measured after releasing the aptamer from the solid phase by, for example, denaturing the double-stranded DNA by NaOH treatment or the like.

Although the sample and labeled aptamer are first mixed and this mixed solution is allowed to react with the immobilized oligonucleotide in the above described method, it is not indispensable to mix the sample and labeled aptamer first, and the three members, that is, the sample, labeled aptamer and immobilized oligonucleotide, may be allowed to react at the same time, or the sample and immobilized oligonucleotide may be allowed to react in advance, and then the aptamer may be allowed to react with the resulting reaction product.

When quantification of the test substance in the sample is carried out, a calibration curve is prepared in advance, the measured signal of SPR or the signal from the label is measured, and the measured value is applied to the calibration curve to carry out the quantification of the test substance in the sample. That is, multiple standard samples containing various different known concentrations of the test substance are prepared, and the above method is applied to these, followed by measurement of the signals of SPR or the signals due to the label bound to the solid phase. The calibration curve is prepared by taking the concentrations of the test substance in the standard samples along the abscissa and the measured signals along the ordinate?. The test substance in an unknown sample can be quantified by carrying out the measurement under the same conditions as in the preparation of the calibration curve, and applying the measurement results to the calibration curve.

As described above, the present invention also provides a novel aptamer molecule having a structure-switching property, and a method for creating it. The novel aptamer molecule having the structure-switching property can be used in the above described method of the present invention, but the aptamer which is capable of being used in the above method of the present invention is not restricted to this aptamer. The novel aptamer molecule of the present invention having the structure-switching property, and the method for creating it will now be described, which description will be considerably overlapping with the above description.

The target substance is not restricted at all as long as an aptamer which specifically binds thereto (that is, binds to the target substance but does not bind to other substances which have structures different from that of the target substance to certain degrees) can be produced, the target substance being the same as the test substance of the method of the present invention described above.

The aptamer molecule of the present invention is an aptamer molecule made of a single nucleic acid, which aptamer molecule has the property to bind to a target substance and hybridizes with an oligonucleotide when it is bound to the target substance, but is incapable of hybridizing with the immobilized oligonucleotide when it is not bound to the target substance. The size of the aptamer used in the present invention is not restricted, and usually about 30-mer to 100-mer, preferably about 50-mer to 70-mer (mer indicates the number of nucleotides). The aptamer may be either DNA or RNA, or another artificial nucleic acid, but is preferably DNA, which is chemically stable and capable of being synthesized easily by automated chemical synthesis. "Made of a single nucleic acid" means that the aptamer is made of a single nucleic acid regardless of whether an intramolecular hybridization exists or not, and therefore an aptamer partially having a double-strand due to hybridization between regions in the molecule is within the scope of an aptamer "made of a single nucleic acid". The binding with the target substance and hybridization with the oligonucleotide preferably occur at room temperature in an aqueous buffer such as water or PBS (which may comprise a surfactant).

The aptamer preferably comprises a loop-like single-stranded region when it is hybridized with the oligonucleotide, and wherein regions adjacent to the both ends of the single-stranded region, respectively, preferably form a double-stranded region. An aptamer is known to comprise the so called "stem-loop structure" like this in many cases, and also known to bind specifically to a target substance mainly through the single-stranded loop structure region. The size of the single-stranded region is not restricted, and usually about 8-mer to 25-mer. The sizes of the regions which are adjacent to the both ends of the single-stranded region and which form the double-stranded region with each other are not restricted, and preferably 2 bp to 10 bp. The secondary structure of the aptamer can be determined easily by a conventional method using a computer. As a software for analysis of the secondary structure of the aptamer, well-known Mfold, for example, can be utilized, which software is freely available in the Mfold web server www.bioinfo.rpi.edu/applications/mfold/dna/).

The oligonucleotide which hybridizes with the above aptamer is not restricted as long as it is an oligonucleotide capable of hybridizing with the aptamer under measurement conditions (described above) when the aptamer is used for measurement of the target substance, and preferably comprises a region which is complementary at least to a consecutive region in the aptamer, of which size is 4-mer to 25-mer, more preferably 8-mer to 25-mer. To achieve an aptamer having a structure-switching property, the combination of the base sequence of the aptamer and the base sequence of the oligonucleotide can be appropriately designed. This will be described in detail later.

The aptamer molecule of the present invention hybridizes with the oligonucleotide when it is bound to a target substance, but the aptamer is incapable of hybridizing with the oligonucleotide when it is not bound to the target substance. That is, the secondary structure and/or tertiary structure of the above aptamer change(s) between the state of being bound to the target substance and the state of being unbound thereto?, and as a result, the aptamer hybridizes with the oligonucleotide when the aptamer is bound to the target substance, but the aptamer is incapable of hybridizing with the oligonucleotide when it is not bound to the target substance.

Such a structure-switching aptamer, which is capable of binding to an arbitrary target substance, can be created by first creating an aptamer which binds to the target substance by the above SELEX method or its modification mentioned below; then intentionally modifying the obtained aptamer such that the above described structure-switching property is exerted; and checking the modified aptamer to confirm that it has the structure-switching property. The method for the intentional modification of the aptamer will be described later in detail.

The aptamer molecule of the present invention having a structure-switching property can be created as follows. First, by the SELEX method or its modification mentioned below, an aptamer which binds to a target substance is created. Since the sizes of the aptamer is usually about 30-mer to 100-mer, a library of nucleic acids having random base sequences of about these sizes is synthesized by an automated nucleic acid synthesizer. In this case, although the full length of the nucleic acid may be a random base sequence, the both end regions of the nucleic acid may also be known base sequences, to make PCR simple when SELEX is carried out. In this case, PCR primers can be hybridized to the regions of these known sequences, respectively. The sizes of the regions which are located in the both end regions of the nucleic acid are not restricted, and usually about 10-mer to 25-mer. In the Examples below, a nucleic acid library of SEQ ID NO:1 was synthesized automatically. Since "N" in SEQ ID NO:1 is an arbitrary base, a nucleic acid library comprising vast kinds of base sequences is formed. In cases where the regions with which the primers hybridize are provided, it is not necessary to determine the base sequence of the aptamer before PCR described later, so that the production process of the aptamer is simplified. However, since the flexibility of the sequence of the aptamer decreases instead, the regions may not be provided.

Subsequently, a target substance immobilized on a solid phase is provided, and the nucleic acid library produced as described above is reacted with the immobilized target substance. The immobilization of the target substance may be carried out simply by physical adsorption of the target substance on a solid phase such as a nitrocellulose membrane, nylon membrane, filter paper, and well of a polystyrene microtiter plate, and in cases where the target substance is a protein, it may also be carried out by covalently bonding the protein to the carrier by utilizing a carboxyl group or amino group of the target substance. The former is simpler. As the conditions of the reaction between the nucleic acid library and the target substance, the same conditions as in the actual measurement of the target substance are preferred, and therefore carrying out the reaction at room temperature is simple and preferred. The reaction time is not restricted, and usually about 1 minute to 30 minutes, preferably about 10 minutes to 20 minutes. Upon reacting with the target substance, aptamers which bind to the target substance are bound to the immobilized target substance and immobilized on the solid phase. On the other hand, nucleic acids which do not bind to the target substance are not bound to the solid phase, and therefore removed by washing.

After removing the nucleic acids which were not bound to the solid phase by washing, the aptamers bound to the immobilized target substance are eluted. The elution can be carried out for example by treating the solid phase with urea at a high concentration of about 6M to 8M. Eluted nucleic acids can be collected by a conventional method such as phenol extraction and/or phenol-chloroform extraction and ethanol precipitation. All the collected aptamers are those bound to the immobilized target substance.

Subsequently, PCR is carried out using the collected aptamers as templates, to amplify the aptamers. In cases where the nucleic acids which were automatically synthesized have the above described primer binding regions in the both end regions, PCR is carried out using those primers. In cases where such primer binding regions are not provided, the base sequences of the collected aptamers are determined, and a pair of PCR primers complementary to their both end regions is synthesized respectively, which primers are used for carrying out PCR. By carrying out asymmetric PCR (one of the pair of primers used in PCR is used in an excess amount), mainly single-stranded nucleic acids can be amplified. Alternatively, single-stranded nucleic acids (the strand which is not biotin-labeled) can be collected from the amplified double-stranded nucleic acids by using a biotin-labeled primer as one of the primers used in PCR; binding the amplified double-stranded nucleic acids to avidin beads; denaturing the nucleic acids in this state by NaOH or the like; and collecting the nucleic acids separated from the beads. By this, since only aptamers which bind to the immobilized target substance are amplified, and the numbers of molecules of the aptamers which bind well to the immobilized target substance and which serve as the templates in PCR are large, the percentages thereof in the amplified nucleic acid library become high.

Subsequently, using the library of the amplified aptamers as the nucleic acid library described above, the above series of steps, that is, a cycle of the series of the steps of: reaction with the immobilized target substance; washing; elution and collection of the aptamers; and amplification by PCR; is repeated about several times to ten and several times. By this, aptamers which bind well to the target substance are concentrated, and aptamers having high binding capacities to the target substance can be obtained.

The present inventors previously invented an improved SELEX, wherein aptamers are allowed to evolve in silico (Non-patent Literature 3). By application of the evolution in silico described in Non-patent Literature 3 to the above described method which is described in Non-patent Literature 2, it is possible to increase the efficiency of creation of desired aptamers. In this method, after finishing the first cycle of the above SELEX, the base sequences of the obtained aptamers are determined, the binding capacities thereof to the target substance are measured, and the measured binding capacities are sorted in the order of the binding capacity. Studies on aptamers to date demonstrated that the basic structure of an aptamer is classified into 4 types, that is, the hairpin type, bulge type, pseudoknot type, and guanine quartet type, and which structure is attained by an aptamer having which base sequence, and which is/are the nucleotide(s) necessary for maintenance of its basic structure, can be easily determined by analysis by a computer. In the method utilizing the evolution in silico described in Non-patent Literature 3, multiple regions of, for example, about 3- to 5-mer, which are not indispensable for maintenance of the basic structure of each aptamer, are exchanged randomly (shuffled) among the respective corresponding regions of the respective obtained aptamers. Thereafter, to the above respective regions after shuffling, random single base substitutions are introduced. Introduction of these shuffling and single base substitutions are carried out in silico. The aptamers having the new base sequences created by the computer are chemically synthesized to obtain the second nucleic acid library, which is then used in the above described cycles. When the second nucleic acid library is prepared, aptamers having regions derived from aptamers with high ranks of the binding capacity are included in the largest amounts, the ratio thereof then being decreased as the rank becomes lower. Thus, by artificially introducing variations by shuffling and random single base substitution in silico, the efficiency of evolution by SELEX can be increased.

The present inventors also invented an improved SELEX, wherein aptamers having higher binding capacities with a target substance can be efficiently obtained in the usual SELEX, and filed a patent application directed thereto (Japanese Laid-open Patent Application (Kokai) No. 2007-14292). By this improved SELEX, aptamers which bind to a desired target substance with high specificity can be created efficiently. In the improved SELEX described in Japanese Laid-open Patent Application (Kokai) No. 2007-14292, when the desired target substance (the target substance in the present invention) is allowed to bind to nucleic acids in a nucleic acid library in the usual SELEX, a carrier on which a non-targeted substance is immobilized is allowed to coexist. Only nucleic acids which bound to the desired target substance are collected, which nucleic acids are then amplified by PCR, and single-stranded nucleic acids are obtained from the amplification product, to obtain a nucleic acid library. The library is brought into contact with a region, on which the target substance is immobilized, and nucleic acids bound to the solid phase are collected and similarly amplified by PCR, to obtain single strands. These single strands are used as a nucleic acid library and again brought into contact with regions on which the target substance and non-targeted substance are immobilized respectively. The cycle is then repeated similarly. By this method, aptamers which bind to the non-targeted substance or carrier are culled, whereas aptamers which specifically bind to the target substance are concentrated, and therefore the aptamers which specifically bind to the target substance can be obtained efficiently.

Subsequently, the aptamers thus obtained are modified so as to have a structure-switching property. This modification is carried out as follows.

First, a region which hybridizes with an oligonucleotide (hereinafter referred to as "hybridization region" for convenience) is added to or inserted into the obtained aptamer molecule, to prepare a modified aptamer molecule. At least a part of the hybridization region herein has a base sequence complementary to another region in the aptamer molecule. Therefore, in the absence of the target substance, the at least a part of the region, which hybridizes with the oligonucleotide, hybridizes with the another region complementary thereto, so that hybridization with the oligonucleotide does not occur. On the other hand, aptamer molecules wherein the intramolecular hybridization is unraveled to make the region which hybridizes with the oligonucleotide is exposed in the presence of the target substance so as to be capable of hybridizing with the oligonucleotide are screened. The term "screening" is used herein because even the aptamer molecules in which the intramolecular hybridization occurs in the absence of the target substance do not necessarily have a structure-switching property, and therefore there are also cases wherein it is necessary to create a certain number of different aptamer molecules and select ones having a structure-switching property therefrom. However, the creation method of the present invention modifies the aptamer intentionally such that a structure-switching property is obtained, and especially in cases where the modification is carried out with the embodiment described later, a desired structure-switching aptamer molecule can be created at a high probability. Therefore, the possibility that the aptamer molecule which was created first has a desired structure-switching property is not low, and in such cases, there exists only the step of confirmation that the aptamer molecule which was created first has a structure-switching property. This is also within the scope of the term "screening" as used herein, even if the number of the type of the aptamer molecules which are checked for whether or not they have a structure-switching property is only one.

To increase the possibility that an aptamer molecule having a structure switching property is obtained, the aptamer molecule preferably comprises a loop-like single-stranded region when the aptamer is hybridized with the oligonucleotide, and wherein regions adjacent to the both ends of the single-stranded region, respectively, preferably form a double-stranded region. Especially, it is preferred that the hybridization region be designed so as to comprise a region complementary to at least a part of the region which hybridizes with the immobilized oligonucleotide, in the loop or in the part extending between the loop and the double-stranded region. Further, the size of the region, which is in the loop or in the part extending between the loop and the double-stranded region, and which is complementary to the at least a part of the region which hybridizes with the immobilized oligonucleotide, is preferably designed to be 3-mer to 10-mer. By designing the hybridization region as described above, the two-dimensional and/or three-dimensional structure(s) of the loop region is/are changed by the intramolecular hybridization in the absence of a target substance. On the other hand, in the presence of the target substance, the loop region structurally altered due to the interaction between the target substance and the aptamer molecule is often chemically more stable in the state where it returns to the structure with which it is capable of binding specifically to the target substance, and binds to the target substance. Therefore, it is highly probable that the intramolecular hybridization is unraveled and the region regains the original loop structure, thereby binding to the target substance. If this occurs, the intramolecular hybridization is unraveled, and the structure of the loop region of the aptamer molecule returns to its original structure. Thus, there is a considerably high possibility that the hybridization region is exposed to enable it to hybridize with the oligonucleotide. That is, by designing the hybridization region as described above, the possibility that an aptamer molecule having a desired structure-switching property is obtained becomes considerably high.

The above modification method will be described concretely referring to the aptamer prepared in the Examples described later.

Figure 1:
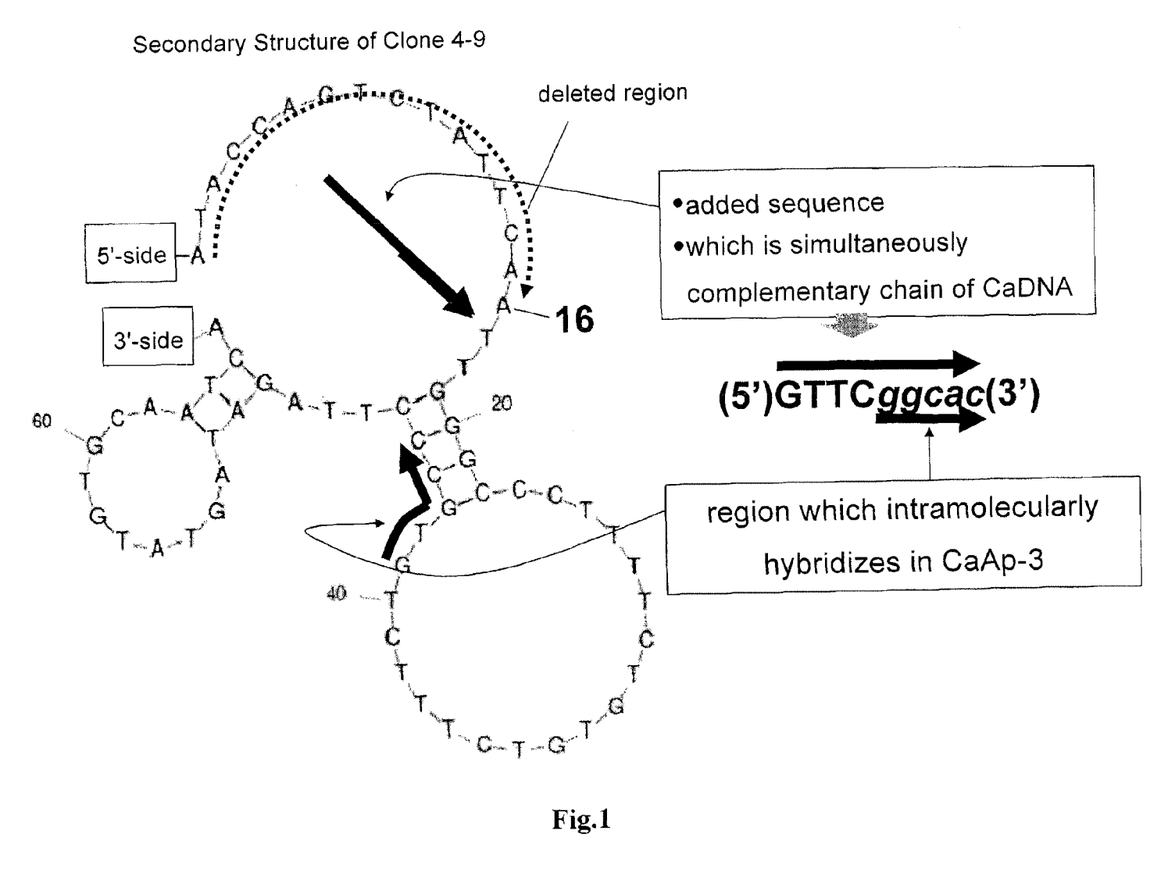
FIG. 1 (SEQ ID NO: 2) is a diagram showing the base sequence and secondary structure of Clone 4-9, which is the aptamer obtained in Example 1 of the present invention and which binds to α-PrP.

First, the base sequence of the aptamer obtained by the above method, which specifically binds to the target substance, is determined by a sequencer or the like, and the secondary structure thereof is determined by a computer. The secondary structure and the base sequence (SEQ ID NO:2) of the aptamer (named "Clone 4-9") created in the Examples below is shown in FIG. 1. As described above, it is known that the basic structures of an aptamers are classified into 4 types, that is, the hairpin type, bulge type, pseudoknot type, and guanine quartet type. Of course, other than the typical forms, there are also ones comprising multiple hairpins (stem-loop structure) or the like, for example. In either case, a region which forms a single-stranded loop is included, and this single-stranded loop region has been shown to be involved in binding with the target substance. Clone 4-9 has two, large and small, stem-loop structures as shown in FIG. 1, and is basically classified as the hairpin type.

It has been shown that the single-stranded loop region is usually involved in binding with the target substance. Therefore, regions which are considered to be unnecessary for maintenance of the loop region (for example, a single-stranded region which is 3 or more bases apart from the end of the stem part of the stem-loop region, and the like) may be deleted at the beginning for simplifying the structure. In the Examples below, the single-stranded region which is 1 nt to 16 nt (16 nt indicates the 16th nucleotide from the 5'-side; the term "nt" will be used in the same way hereinafter) from the 5' of Clone 4-9 was deleted. The fact that the stem-loop structure is maintained even after the deletion of this region can be known by an analysis using a computer, and the maintenance of the binding capacity was also confirmed by a binding assay.

Since it is known, as described above, that the single-stranded loop region is involved in the binding with the target substance, in the modification method of the aptamer which was developed by the present inventors, in the absence of the target substance, at least a part of the region which binds to the immobilized oligonucleotide hybridizes intramolecularly with the loop region or the region extending between the loop region and the stem region (double-stranded region) adjacent thereto, thereby making the aptamer incapable of binding to the immobilized oligonucleotide. That is, a region having a base sequence, at least a part of which sequence is complementary to the loop region or the region extending between the loop region and the stem region (double-stranded region) adjacent thereto, is added as the hybridization region for the immobilized oligonucleotide. This hybridization region can be added to, for example, the 5'-end of the aptamer. In the Examples below, as shown in FIG. 1, the region of 1nt to 16 nt of Clone 4-9 was deleted, and the hybridization region of GTTCggcac (SEQ ID NO:3) was then added (indicated as an arrow in FIG. 1) to the 5'-end (the 17 nt of Clone 4-9) after the deletion. This hybridization region hybridizes with the immobilized oligonucleotide, and therefore the immobilized oligonucleotide corresponds to the complementary strand of the base sequence indicated by the SEQ ID NO:3. The size of the hybridization region for the immobilized oligonucleotide is usually 4-mer to 25-mer, preferably about 8-mer to 25-mer. In the hybridization region shown in FIG. 1, the lower-cased part, ggcac, is complementary to the region of the 41 nt to 45 nt in Clone 4-9 (indicated as an arrow in FIG. 1), and meant to hybridize with this region intramolecularly. The upper-cased part, GTTC, was added as a sequence which is not involved in the intramolecular hybridization, since the lower-cased ggcac part alone was considered to be insufficient to hybridize with the immobilized DNA. When the aptamer is brought into contact with the target substance, it needs to be unfolded to allow the hybridization region for the immobilized oligonucleotide to become single-stranded, and therefore an intramolecular hybridization which is too firm is not appropriate. Thus, the size thereof is usually about 3-mer to 10-mer, preferably about 4-mer to 6mer.

Figure 2:
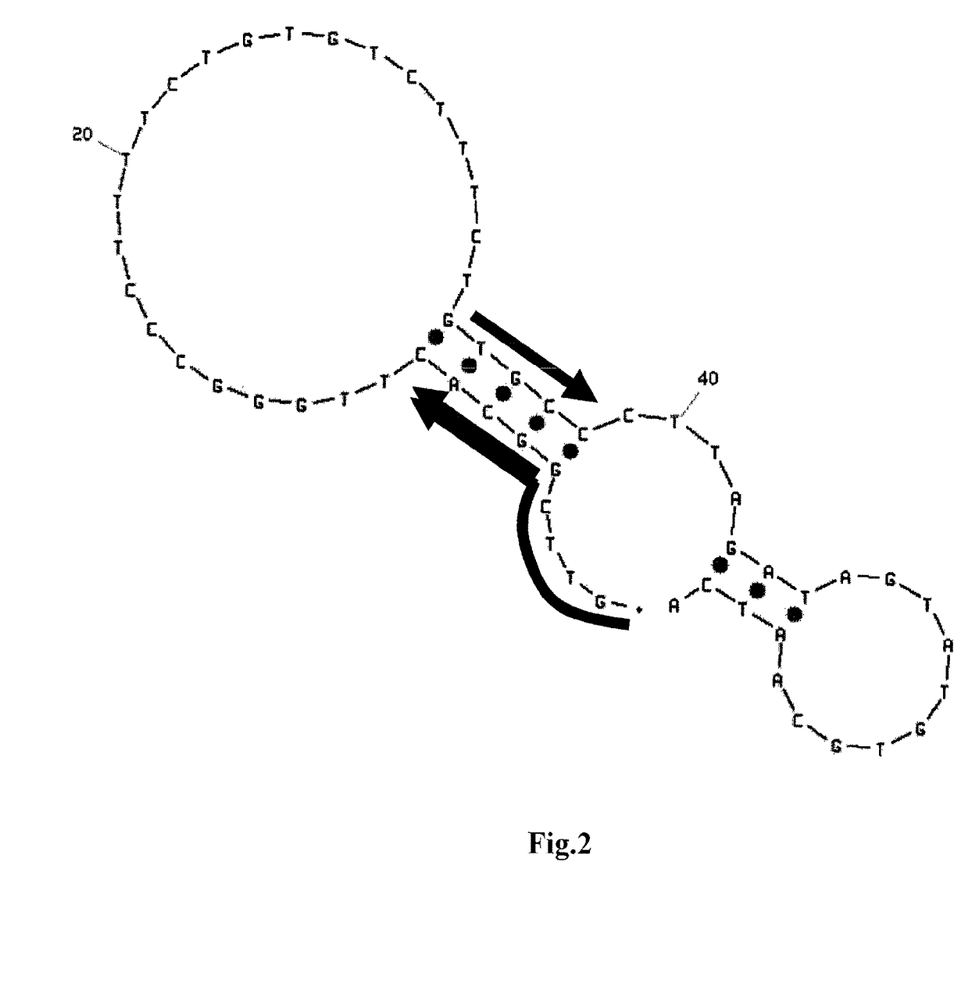
FIG. 2 (SEQ ID NO: 7) is a diagram showing the secondary structure of the α-PrP-binding aptamer in the absence of α-PrP, which aptamer was synthesized in Example 1 of the present invention and which has a structure-switching property.

The aptamer designed as above (named "CaAp-3") (SEQ ID NO:7) has the secondary structure shown in FIG. 2 in the absence of a target substance ($\alpha$-PrP) (the secondary structure of an aptamer after modification can also be analyzed by a computer). On the other hand, upon being brought into contact with the target substance, the above described intramolecular hybridization is unraveled according to the interaction with the target substance, thereby allowing the aptamer to have the secondary structure as shown in FIG. 1. This allows the hybridization region for the immobilized oligonucleotide to become single-stranded and exposed, enabling hybridization thereof with the immobilized oligonucleotide.

Subsequently, the aptamer modified as above is experimentally checked for whether or not it actually has a structure-switching property. This can be carried out, for example, as described in the Examples below, as follows. First, the target substance is immobilized on a sensor chip for SPR, which is then brought into contact with an aptamer solution, to confirm that the aptamer maintains the binding capacity to the target substance. The above immobilized oligonucleotide is then immobilized on the sensor chip for SPR, and a solution containing the aptamer solely and a mixed solution of the aptamer and target substance are brought into contact with the sensor chip respectively, wherein the above checking can be carried out by confirming that the aptamer does not bind to the immobilized oligonucleotide in the case of the sole aptamer, whereas the aptamer binds to the immobilized oligonucleotide in the case of the mixed solution of the aptamer and target substance. Alternatively, instead of using SPR, the aptamer may be labeled, and the binding thereof to the solid phase may be checked by measuring the label bound to the solid phase. If the result of the checking showed that a structure-switching property was not obtained, an aptamer, wherein the intramolecular hybridization region was changed to another site, is synthesized, and experimentally checked as described above. That is, an aptamer molecule having a structure-switching property is screened.

By the above method, CaAp-3, which has the base sequence shown in SEQ ID NO:7, whose target substance is $\alpha$-PrP, and which has a structure-switching property, was obtained. As concretely indicated in the Examples below, this structure-switching aptamer also binds to $\beta$-PrP. Although the spatial structure is different between $\alpha$-PrP and $\beta$-PrP (the former is mainly in the $\alpha$-helix form, and the latter is mainly in the $\beta$-sheet form), their amino acid sequences are completely the same. From the fact that the aptamer binds to both $\alpha$-PrP and $\beta$-PrP, the aptamer is thought to bind to relatively small target regions having the same amino acid sequences in the both proteins, and therefore the above described structure-switching property is considered to be exerted also with $\beta$-PrP. An aptamer which binds to both $\alpha$-PrP and $\beta$-PrP is useful for measurement of the infectious type (abnormal type) prion. More particularly, $\alpha$-PrP, that is, a prion of the wild type (normal type), is degraded upon treatment with a serine protease, but $\beta$-PrP is not degraded. Therefore, a sample containing a prion is treated with a serine protease, and if the prion is detected in the sample after the treatment, the detected prion can be determined to be an infectious type (abnormal type). Currently, an immunoassay kit which uses an antibody that binds to both the infectious type (abnormal type) and wild type (normal type), and which detects only an infectious type (abnormal type) prion by the above method, is practically used. By using CaAp-3 of the present invention, a kit for measurement of a prion, which is similar to such an immunoassay kit, can be provided. Since, as described above, an aptamer can be obtained simply by chemical synthesis, and does not require complicated purification, it is cost advantageous compared to an antibody. Further, in an widely-used sandwich immunoassay method such as sandwich ELISA, two kinds of antibodies, which undergo antigen-antibody reaction with a prion, are necessary, but, in the case of an aptamer, only a single kind of aptamer and a short immobilized oligonucleotide are required, therefore the aptamer being advantageous also in this respect compared to the immunoassay.

Further, an aptamer having the same base sequence as shown in SEQ ID NO:7 except that one or several bases are substituted and/or deleted and/or inserted and/or added, which aptamer exerts a structure-switching property with $\alpha$-PrP, can also be used for the measurement of a prion in the same manner as CaAp-3. In this case, the total number of the substitution, deletion, insertion and addition is 1 to several (up to 9), preferably 1 to 5. The substitution, deletion, insertion and addition are preferably carried out in regions which are not responsible for binding with the target substance, and preferably carried out at the end of the aptamer or in the vicinity thereof, at least in regions other than the stem-loop region. Especially, in regions other than the stem-loop region, deletion of 1 to several nucleotides at the end of the aptamer and addition of 1 to several nucleotides to the end are considered not to affect the structure-switching.

Incidentally, Clone 4-9 having the base sequence shown in SEQ ID NO:2, as well as the 17 nt-66 nt fragment and 19 nt-66 nt fragment thereof, does not have a structure-switching property, but bind to both α-PrP and β-PrP. Thus, these can be utilized as alternatives to the antibody that binds to both α-PrP and β-PrP. Since an aptamer can be synthesized simply by chemical synthesis, does not require purification, and is less expensive compared to an antibody, it will be advantageous if the antibody can be replaced by an aptamer. Further, as described above, an aptamer having the same base sequence as shown in SEQ ID NO:2 except that one or several bases are substituted and/or deleted and/or inserted and/or added, which aptamer binds to α-PrP and β-PrP, can also be utilized as an alternative to the anti-prion antibody. In this case, as described above, the total number of the substitution, deletion, insertion and addition is 1 to several (up to 9), preferably 1 to 5. The substitution, deletion, insertion and addition are preferably carried out in regions which are not responsible for binding with the target substance, and preferably carried out at the end of the aptamer or in the vicinity thereof, at least in regions other than the stem-loop region. Especially, in regions other than the stem-loop region, deletion of 1 to several nucleotides at the end of the aptamer and addition of 1 to several nucleotides to the end are considered not to affect the structure-switching.

That is, (1) the aptamer having the base sequence shown in SEQ ID NO:2, (2) the aptamer consisting essentially of the 17 nt to 66 nt of the base sequence of SEQ ID NO:2, (3) the aptamer consisting essentially of the 19 nt to 66 nt of the base sequence of SEQ ID NO:2, (4) aptamers having the same base sequences as the base sequences of the above (1)-(3) except that one or several bases are substituted and/or deleted and/or inserted and/or added, which aptamers bind to α-PrP and β-PrP, can be used for measurement of α-PrP and β-PrP. Since, as described above, α-PrP is degraded by a serine protease, if a sample after treatment by a serine protease is provided for measurement, only β-PrP, which is not degraded by the serine protease, can be measured.

The aptamer molecule of the present invention having a structure-switching property can be used for measurement of a target substance. The measurement of the target substance using the aptamer molecule of the present invention can be carried out as described above, for example as follows.

First, the target substance in a sample is brought into contact with the above aptamer. This can be carried out by mixing the sample with an aptamer solution and incubating the resulting mixture. When the target substance is quantified, it is preferred that the aptamer in an excess amount with respect to the expected amount of the target substance in the sample be allowed so as to react to bind the total target substance to the labeled aptamers. The condition of the incubation is not restricted, and simply and preferably carried out at room temperature. The reaction time is not restricted, and usually about 1 minute to 30 minutes, preferably about 10 minutes to 20 minutes.

Subsequently, the mixed solution of the sample and aptamer is brought into contact with the above described oligonucleotide immobilized to the solid phase. This can be carried out by mixing the above described carrier, on which the oligonucleotide is immobilized, with the mixed solution of the sample and aptamer, and incubating the resulting mixture. Alternatively, in cases where the carrier on which the oligonucleotide is immobilized is in the form of a column or filter, it may also be carried out simply by allowing the mixture to pass through the column or filter. When the target substance is quantified, the immobilized oligonucleotide is preferably in an excess amount with respect to the expected amount of the target substance in the sample subjected to the measurement (that is, an amount, with which the total amount of the target substance in the sample subjected to the measurement can be bound to the immobilized oligonucleotide via the aptamer). The incubation is simply and preferably carried out at room temperature similarly to the condition employed in the modification of SELEX when the aptamer was created. The reaction time is not restricted, and usually about 1 minute to 30 minutes, preferably about 10 minutes to 20 minutes. After this incubation, the solid phase is washed to remove the aptamer which was not bound to the solid phase. In cases where the measurement is carried out by SPR, the above incubation is not necessary since SPR can measure the binding in real time.

The method to immobilize an oligonucleotide on a solid phase is well known, and can be carried out by a conventional method. For example, by covalently bonding biotin to one end of an oligonucleotide while immobilizing avidin on a carrier, it is possible to bind the oligonucleotide to the carrier via the avidin-biotin bond, whereas the method is not restricted thereto, and the oligonucleotide can also be directly and covalently bound to the carrier by a method such as the glutaraldehyde crosslinking method. It may also be physically adsorbed on such as a membrane made of nylon or nitrocellulose which adsorbs DNA well. The oligonucleotide may also be directly bound to the carrier, or may be bound to the carrier via a low molecular weight compound such as biotin. Further, the oligonucleotide may also be bound to the carrier via a spacer. For example, a longer oligonucleotide comprising in its one end the oligonucleotide to be immobilized may also be prepared, the end, which is opposite to the oligonucleotide to be immobilized, being bound to the carrier via the above described biotin-avidin bond or the like. In this case, in the nucleic acid immobilized on the carrier, the polynucleotide moiety other than the oligonucleotide to be immobilized simply acts as a spacer, and therefore the base sequence and the size thereof are not restricted at all. As for the carrier used as the solid phase, one conventionally used for immobilization of nucleic acids can be used as it is. For example, avidin beads, wherein avidin was immobilized on beads made of a macromolecule such as a synthetic resin or agarose, are commercially available, and therefore a commercial product can be used as it is. Alternatively, a commercially available substrate for a DNA chip such as one made of glass, silicon, and a synthetic resin can also be used. As for the carrier like this, one in the form of a column, like one used in chromatography, or one in the form of a filter can also be employed in addition to ones in the form of beads or a plate. Alternatively, in cases where the measurement is carried out by SPR, a sensor chip for SPR can be used as the solid phase. Also in this case, as described above, the sensor chip, on which avidin or streptavidin was immobilized, is commercially available, and therefore, by binding biotin to one end of the oligonucleotide, the oligonucleotide can be immobilized on the sensor chip via the avidin-biotin bond.

If the target substance is contained in the sample, the target substance is bound to the aptamer. The aptamer bound to the target substance hybridizes with the immobilized oligonucleotide, and is bound to the solid phase as described above. On the other hand, the aptamers which did not bind to the target substance is removed by washing since it is not capable of hybridizing with the immobilized oligonucleotide.

In the next step, the aptamer bound to the solid phase is measured. As described above, the aptamer bound to the solid phase is the aptamer bound to the target substance, and therefore measurement of the aptamer bound to the solid phase allows measurement of the target substance in the sample.

The measurement of the aptamer bound to the solid phase can be carried out for example by SPR as described in the Examples below. In this case, the above method can be carried out by using a sensor chip for SPR, on which the oligonucleotide was immobilized, as the above solid phase. Alternatively, as described above, the aptamer bound to the solid phase can also be measured by using labeled aptamer and measuring the label bound to the solid phase. Labeling of the aptamer molecules of the present invention allows measurement of the target substance by a method similar to that of a well-known immunoassay. The present invention also provides labeled aptamer molecules wherein the aptamer molecules of the present invention were labeled. As for the label, well known labels conventionally used in immunoassays can be employed, and, for example, enzyme labels, fluorescent labels, chemiluminescent labels, radioactive labels, gold colloid labels and the like can be employed. These labels may be attached to the aptamer by a conventional method after preparing the aptamer, and the labeled aptamer can also be obtained by using, as a primer for PCR which is carried out during the preparation process of the aptamer by SELEX described below, a primer having a label attached to its end (the end corresponding to the end of the polynucleotide being amplified). The label is preferably attached to one end or its vicinity of the aptamer so as not to interfere with the specific binding between the aptamer and the target substance. Labeling of the aptamer is preferred since it makes measurement of the aptamer bound to the solid phase easy, but labeling is not indispensable because the aptamer bound to the solid phase can be measured by the surface plasmon resonance (SPR) method as described in the Examples below even in cases where the aptamer is not labeled. Measurement of the labels can also be carried out by conventional methods for these respective labels. For example, in cases where the label is a fluorescent label, the fluorescence intensity of the label bound to the solid phase is measured. In cases where the label is a chemiluminescent label or radioactive label, the luminescence intensity or intensity of radioactivity bound to the solid phase is measured. In cases where the label is an enzyme, a substrate necessary for an enzyme reaction is added, and the product yielded by the enzyme reaction is measured. In case of an enzyme which catalyzes an electrochemical reaction, a working electrode, counter electrode, and reference electrode are immersed in a solution to which a substrate of the enzyme was added, and the electromotive force induced between the working electrode and counter electrode is measured. This is the same as the measurement of an enzyme reaction using a conventional enzyme electrode, and can be carried out easily by a conventional method. In cases where the enzyme reaction product is a colored substance, the product can be measured by measuring the absorbance of the reaction solution. In cases where one desires to measure a label in the free state when the label bound to the solid phase is measured, the label may be measured after releasing the aptamer from the solid phase by, for example, denaturing the double-stranded DNA by NaOH treatment or the like.

Although the sample and labeled aptamer are first mixed and this mixed solution is allowed to react with the immobilized oligonucleotide in the above described method, it is not indispensable to mix the sample and labeled aptamer first, and the three members, that is, the sample, labeled aptamer and immobilized oligonucleotide, may be allowed to react at the same time, or the sample and immobilized oligonucleotide may be allowed to react in advance, and then the aptamer may be allowed to react with the resulting reaction product.

When quantification of the target substance in the sample is carried out, a calibration curve is prepared in advance, the measured signal of SPR or the signal from the label is measured, and the measured value is applied to the calibration curve to carry out the quantification of the target substance in the sample. That is, multiple standard samples containing various different known concentrations of the target substance are prepared, and the above method is applied to these, followed by measurement of the signals of SPR or the signals due to the label bound to the solid phase. The calibration curve is prepared by taking the concentrations of the target substance in the standard samples along the abscissa and the measured signals along the ordinate. The target substance in an unknown sample can be quantified by earring out the measurement under the same conditions as in the preparation of the calibration curve, and applying the measurement results to the calibration curve.

The present invention will now be described more concretely by way of Examples below. However, the present invention is not restricted to the Examples below.

EXAMPLE 1

1. Preparation of α-PrP-binding Aptamer
   By the modification of SELEX described in Japanese Laid-open Patent Application (Kokai) No. 2007-14292, an α-PrP-binding aptamer was created as follows.
   (1) That is, first, DNA having the base sequence shown in SEQ ID NO:1 was chemically synthesized by an automated DNA synthesizer. "N" in SEQ ID NO:1 is an arbitrary base, and, by the automated DNA synthesizer, a library of single-stranded DNAs was constructed, wherein the region, which is represented by the continuous Ns in SEQ ID NO:1 has a random base sequence. The single stranded DNAs were dissolved in binding buffer (10 mM Tris-HCl, pH 7.4, 100 mM KCl) to a concentration of 1 nmol/100 µl, and heated at 95° C. for 3 minutes, followed by cooling of the solution slowly to the room temperature of 25° C., thereby allowing folding of the DNAs. The prepared single-stranded DNA solution was diluted to 3000 µl with the binding buffer, and the protein was immobilized.
   (2) On a nitrocellulose membrane, α-PrP and Zif268 which is a kind of transcription protein were adsorbed on separate sites. This nitrocellulose membrane was incubated with a solution of the DNA random library prepared in (1) (the total DNA concentration was 500 nM in the first round, 40 nM in the second round, 20 nM in the third round, and 5 nM in the fourth round) at room temperature for 1 hour. The buffer for the solution used at this time was PBS-T (PBS containing 0.05% Tween 20 (trade name)) (in any operation below, the buffer used was PBS-T unless otherwise specified). After the incubation, the solution was discarded, and the nitrocellulose membrane was further washed several times with PBS-T.
   (3) By reacting 7 M urea solution with α-PrP on the nitrocellulose membrane, the DNAs bound thereto were eluted.

This was subjected to phenol-chloroform extraction and ethanol precipitation according to a conventional method, thereby collecting the DNA.

(4) Using, as the template, the collected DNAs, and a pair of primers having the base sequences complementary to the respective regions other than "n" in SEQ ID NO: 1, PCR (40 cycles of: denaturation at 94° C. for 34 seconds, annealing at 46° C. for 30 seconds, and extension reaction at 72° C. for 30 seconds) was carried out to amplify the DNA. The obtained amplified double-stranded DNA was added to avidin-immobilized beads, and eluted by 0.15 M NaOH to prepare single-stranded DNA.

Using the amplified single-stranded DNA library as the template, the above cycle of (2)-(4) was repeated 4 times. As a result, as the aptamer amplified best, that is, bound to α-PrP best, the aptamer having the base sequence shown in SEQ ID NO:2 was obtained. This aptamer was named Clone 4-9.

2. Characterization of Clone 4-9 and Fragments Thereof

The secondary structure of Clone 4-9 (SEQ ID NO:2) was analyzed by a computer (analysis software: Mfold, URL: http://www.bioinfo.rpi.edu/applications/mfold/dna/). The result is shown in FIG. 1. In the case of an aptamer having a stem-loop structure, it is known that the loop region is usually involved in binding with a target substance. Thus, it was assumed that the region upstream of the 18 nt, which is 3 bases upstream of the root part of the first stem-loop structure from the 5'-side, is not involved in the binding with α-PrP. Therefore, the aptamer, wherein the 1 nt-18 nt of Clone 4-9 were deleted, was synthesized by an automated DNA synthesizer. This aptamer was named "Clone 4-9 (19-66)". Further, an aptamer in which the region (i.e., 47 nt to 66 nt of Clone 4-9) downstream of the first stem-loop structure was further deleted was also synthesized. This aptamer was named "Clone 4-9(19-46)".

The binding capacities of Clone 4-9, Clone 4-9 (19-66), and Clone 4-9 (19-46) to α-PrP were measured by SPR. That is, α-PrP was immobilized on the sensor chip CM5 (trade name; commercially available from BIACORE; a chip wherein carboxymethyldextran was immobilized on the surface of a thin layer of gold) by covalently bonding it to the chip via its amino group. After heat treatment of 2 μM Clone 4-9 at 95° C., it was slowly cooled to 25° C. for 30 minutes, thereby allowing folding of Clone 4-9. BIACORE X, commercially available from BIACORE, was used in SPR. PBS was used as the running buffer, and 0.05% SDS was used for regeneration. To a sensor chip on which about 10000 RU (resonance units) of α-PrP was immobilized, 50 μl of various concentrations of Clone 4-9 solution was injected, and their interaction was measured at room temperature. The measurement was carried out at a flow rate of 10 μL/min., using PBS buffer (pH 7.0). The above described Clone 4-9 (19-66) and Clone 4-9 (19-46) were also similarly subjected to the experiment. However, this was carried out at a flow rate of 20 μL/min.

Figure 3:
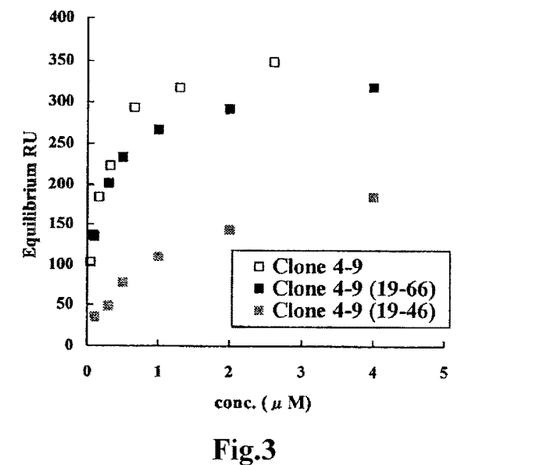
FIG. 3 is a diagram showing the result of the binding test by SPR between: Clone 4-9 and fragments thereof; and α-PrP, respectively.

The results are shown in FIG. 3. As shown in FIG. 3, with respect to Clone 4-9 (19-66), a signal almost at the same level with that of Clone 4-9 was obtained, thereby confirming that Clone 4-9 (19-66) binds to α-PrP. However, a slight decrease in the binding capacity was observed. The sequence TT (17-18 nt and 47-48 nt) exists at the both ends of the stem-loop structure of the 19-66 nt in Clone 4-9. The sequence TT at both ends of a stem-loop structure sometimes stabilizes the stem-loop structure. Thus, considering that the slight decrease in the binding capacity of Clone 4-9 (19-66) was due to the deletion of the sequence TT, creation of an aptamer having a desired structure-switching property was carried out by modification of Clone 4-9 (17-66), wherein the sequence TT is remaining.

3. Modification of Aptamer

Clone 4-9 (17-66) was modified as described above. That is, as shown in FIG. 1, a DNA wherein the oligonucleotide having the base sequence shown in SEQ ID NO:3 was added to the 5'-end of Clone 4-9 (17-66), was synthesized. The added region having the base sequence shown in the SEQ ID NO:3 is the region which hybridizes with the immobilized oligonucleotide, and the immobilized oligonucleotide is the complementary strand of this region. In the bases sequence shown in SEQ ID NO:3, ggcac in the 3'-side is complementary to the 41 nt-45 nt of Clone 4-9, which is indicated by an arrow in FIG. 1, the ggcac hybridizing intramolecularly with this region in the absence of α-PrP (see FIG. 2). As described above, the aptamer obtained by this modification is named CaAp-3, and the base sequence thereof is shown in SEQ ID NO:7.

Similarly, CaAp-1 having the base sequence shown in SEQ ID NO:4, and CaAp-2 having the base sequence shown in SEQ ID NO:5, were synthesized. In both CaAp-1 and CaAp-2, the 6 bases in the 3'-side of the region added to the 5'-end, that is, acagaa, correspond to the complementary strand of the 27 nt-32 nt and 37 nt-42 nt of the clone 4-9 shown in FIG. 1 (the 27 nt-32 nt and 37 nt-42 nt of the clone 4-9 are both ttctgt). Also in these cases, the first loop from the 5'-side is designed to be broken by intramolecular hybridization in the absence of α-PrP.

4. Measurement of the Binding Capacity of the Aptamer

The binding capacity of each of the 3 kinds of synthesized aptamers to α-PrP was measured in the same manner as in the above 2, by SPR. The results are shown in FIG. 4.

Figure 4:
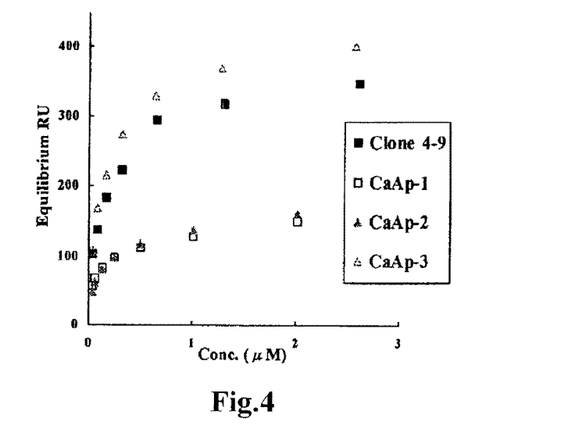
FIG. 4 is a diagram showing the result of the binding test by SPR between: the 3 kinds of aptamers synthesized in Example 1 of the present invention and Clone 4-9; and α-PrP, respectively.

As shown in FIG. 4, each of the 3 kinds of synthesized aptamers shows an increase in the SPR intensity (equilibrium resonance unit (RU)) in a concentration-dependent manner, indicating that they have the binding capacity with α-PrP. Especially, CaAp-3 has a binding capacity comparable to or higher than that of Clone 4-9 before modification, and the binding affinity thereof to α-PrP was highest among the 3 kinds of aptamers. On the other hand, the binding affinities of CaAp-1 and CaAp-2 to α-PrP decreased to a considerable degree compared to that of Clone 4-9 before modification, indicating that CaAp-3 is the best of these 3 kinds. From the Scatchard plot prepared from the result for CaAp-3, Kd=116 nM was obtained.

5. Quantification of α-PrP Using CaAp-3

The complementary strand (CaDNA-3, SEQ ID NO:6) of the 9 bases (SEQ ID NO:3) at the 5'-end of CaAp-3 was immobilized on a sensor chip for SPR. That is, biotin was bound to the 3'-end of the oligonucleotide having the base sequence shown in SEQ ID NO:6, and the oligonucleotide was immobilized on the sensor chip for SPR, on which surface avidin had been immobilized, by utilizing avidin-biotin bonding.

Multiple standard solutions containing 0.1 μM CaAp-3 and various concentrations ranging 0-1.00 μM of α-PrP were prepared. Each of these was injected to measure interaction at room temperature. The measurement was carried out at a flow rate of 20 μL/min., using PBS buffer (pH 7.0).

Figure 5:
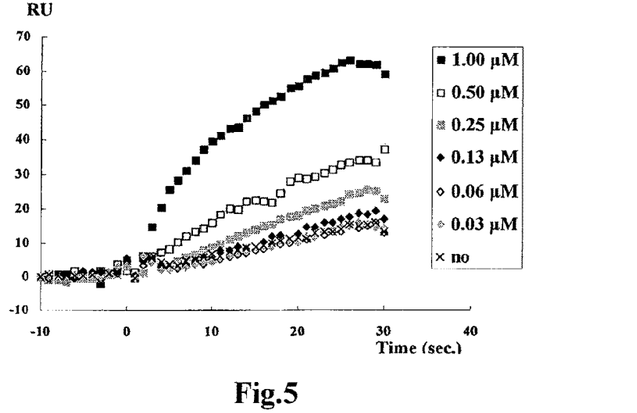
FIG. 5 shows the result of the measurement of various concentrations of α-PrP by SPR, according to the method of the present invention using the aptamer CaAp-3, which was synthesized in Example 1 of the present invention as the aptamer.

The results are shown in FIG. 5. As shown in FIG. 5, the value of RU at equilibrium increased in a concentration-dependent manner, indicating that α-PrP can be quantified by the above method.

EXAMPLE 2

Quantification of α-PrP by ELISA Using CaAp-3

CaDNA-3-11T wherein the thymine-oligo DNA of 11-mer was inserted into the 5'-end of CaDNA-3 (SEQ ID NO:6) as the spacer, was used as the immobilized DNA. After immobilizing 0.1 µM Ca DNA-3-11T (100 µL) on a streptavidin-coated plate, blocking was carried out with 1% skim milk. Various concentrations of α-PrP or BSA was mixed with 0.1 µM CaAp-3 (final concentration), and the resulting mixture was incubated at room temperature for 30 minutes. To the DNA-immobilized plate, 100 µL of this incubated sample was added, which sample was then incubated at room temperature for 2 hours. Thereafter, washing was carried out 4 times with 200 µL of PBS-T (0.05% tween20 (trade name)), and fluorescence measurement was carried out. PBS-T was also used for preparation of the sample.

Figure 6:
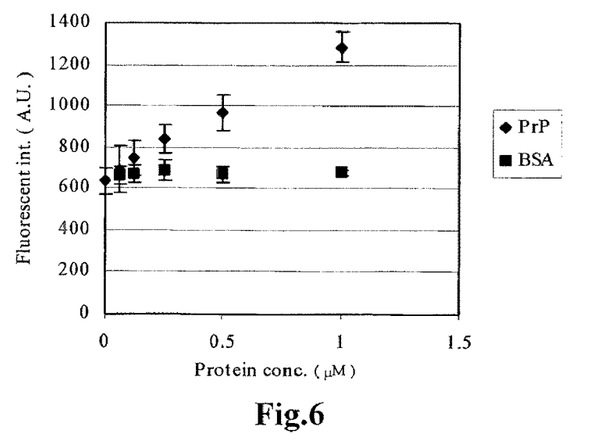
FIG. 6 shows the result of measurement of various concentrations of α-PrP by the method similar to ELISA, according to the method of the present invention, which was carried out in Example 2 using the aptamer CaAp-3 as the aptamer.

The result of the fluorescence measurement is shown in FIG. 6. The fluorescence intensity changed in a manner dependent on the concentration of α-PrP. On the other hand, in the case of the control BSA, the fluorescence intensity did not change depending on the concentration. Thus, it was shown that the target molecule can be quantified by this plate assay.

Figure 7:
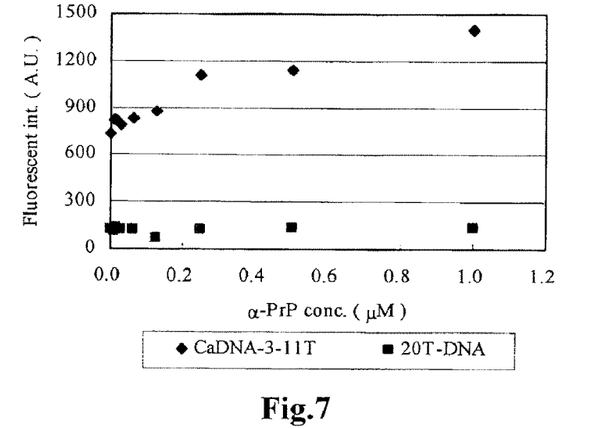
FIG. 7 shows the result of the control experiment of Example 2 using the aptamer CaAp-3 as the aptamer and using the thymine-oligo DNA of 20-mer, which does not have complementarity to the aptamer CaAp-3, as the immobilized oligonucleotide.

As a supplement, the result of a control experiment, which was carried out using the thymine-oligo DNA of 20-mer instead of CaDNA-3, is shown in FIG. 7. As shown in FIG. 7, when 20T-DNA was used, a high fluorescence intensity was not observed, thereby confirming that nonspecific binding of CaAp-3 and CaDNA-3 to α-PrP did not occur.

EXAMPLE 3

Confirmation of Structural Change of CaAp-3 by Gel Shift Assay

CaAp-3 and CaDNA-3, which were FITC-labeled at their 5'-ends, were used. α-PrP and CaAp-3 were mixed and left to stand at room temperature for not less than minutes. Then CaDNA-3 was added thereto, and the resulting mixture was left to stand at room temperature for another not less than 15 minutes. Sample preparation was carried out using 150 mM NaCl and 20 mM phosphate buffer, and the samples were mixed to achieve the final concentrations of 4 µM α-PrP, 400 nM CaAp-3, and 400 nM CaDNA-3. Polyacrylamide gel electrophoresis was carried out using the prepared mixed sample, and the obtained gel was subjected to fluorescence scanning. As a control experiment, the same experiment was carried out, except that, instead of each sample, the buffer for the sample preparation was mixed. Electrophoresis was carried out with PhastSystem (GE Healthcare Science), using a 8-25% gradient gel.

Figure 8:
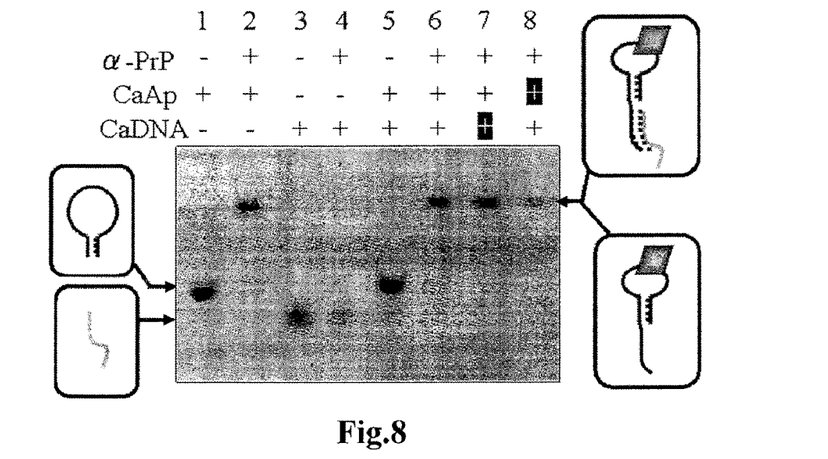
FIG. 8 is a diagram showing the result of the gel shift assay, which was carried out in Example 3 using the aptamer CaAp-3.

The results of the gel shift assay are shown in FIG. 8. In FIG. 8, black bands indicate the fluorescence of FITC. Each mixed sample is shown above the gel shift image. "+" in white indicates that the DNA was FITC-unlabeled. In contrast to the band in lane 1 showing only CaAp-3, the band shift due to the complex between CaAp-3 and α-PrP was observed in lane 2. With respect to the mixed sample in lane 6, wherein CaDNA-3 was further added to the mixed sample in lane 2, the band shift almost at the same level as in lane 2 was observed. However, according to the control experiments in lanes 7 and 8, it was shown that the band observed in this lane 6 was composed of 3 kinds of samples, α-PrP, CaAp-3, and CaDNA-3. Therefore, the result of this gel shift assay supports that CaAp-3 undergoes the structural change due to recognition of α-PrP, thereby hybridizing with CaDNA-3. The reason why no difference was observed in band shift between lane 2 and lanes 6, 7, and 8 is considered to be that CaDNA-3 is a small oligo DNA of 9 bases.

The invention claimed is:

1. A method for measuring a test substance in a sample, said method comprising:
   simultaneously or sequentially bringing an aptamer, said test substance in said sample and a solid phase on which an oligonucleotide is immobilized, into contact with each other, said aptamer having a property to bind to said test substance, said aptamer hybridizing with said oligonucleotide immobilized on said solid phase when it is bound to said test substance, said aptamer having at least some intramolecular hybridization when it is not bound to said test substance, which prevents said aptamer from being able to hybridize with said immobilized oligonucleotide when said aptamer is not bound to said test substance; and
   measuring said aptamer bound to said solid phase, after washing.

2. The method according to claim 1, wherein said aptamer is labeled, and the measurement of said aptamer bound to said solid phase is carried out by measuring said label.

3. The method according to claim 1 or 2, wherein said aptamer comprises a loop-like single-stranded region when said aptamer is hybridized with said oligonucleotide, and wherein regions adjacent to the both ends of said single-stranded region, respectively, form a double-stranded region by intramolecular hybridization when said aptamer is not bound to said test substance.

4. The method according to claim 3, wherein said aptamer comprises a region located in said loop-like single-stranded region or at a portion extending between said loop-like single-stranded region and said double-stranded region, complementary to at least a part of said aptamer which hybridizes with said immobilized oligonucleotide.

5. The method according to claim 4, wherein said region complementary to at least a part of said aptamer which hybridizes with said immobilized oligonucleotide, and that is located in said loop-like single-stranded region or at a portion extending between said loop-like single-stranded region and said double-stranded region, has a size of 3-mer to 10-mer.

6. The method according to claim 1, comprising mixing said aptamer and said test substance, and then bringing the resulting mixture into contact with said solid phase.

7. The method according to claim 1, wherein the aptamer is CaAp-3 comprising SEQ ID NO:7.

8. The method according to claim 1, wherein the aptamer comprises SEQ ID NO:1.

* * * * *